US007420000B2

(12) United States Patent
Petasis

(10) Patent No.: US 7,420,000 B2
(45) Date of Patent: Sep. 2, 2008

(54) AMINO PHOSPHONATE AND AMINO BIS-PHOSPHONATE DERIVATIVES

(75) Inventor: Nicos A. Petasis, Hacienda Heights, CA (US)

(73) Assignee: University of Southern California, Los Angeles, CA (US)

(*) Notice: Subject to any disclaimer, the term of this patent is extended or adjusted under 35 U.S.C. 154(b) by 91 days.

(21) Appl. No.: 10/938,256

(22) Filed: Sep. 10, 2004

(65) Prior Publication Data

US 2005/0234021 A1  Oct. 20, 2005

Related U.S. Application Data

(60) Provisional application No. 60/501,937, filed on Sep. 10, 2003.

(51) Int. Cl.
*A61K 31/34* (2006.01)
*C07F 3/06* (2006.01)

(52) U.S. Cl. .................. 514/461; 549/218; 549/74; 548/561; 546/329; 514/76; 514/357; 514/427; 514/428; 514/438; 514/469; 514/443

(58) Field of Classification Search .............. 514/76, 514/357, 427, 428, 438, 469, 443, 461; 546/329; 548/561; 549/49, 74, 218
See application file for complete search history.

(56) References Cited

U.S. PATENT DOCUMENTS

| | | | |
|---|---|---|---|
| 3,710,795 A | 1/1973 | Higuchi et al. | |
| RE28,819 E | 5/1976 | Thompson | |
| 4,044,126 A | 8/1977 | Cook et al. | |
| 4,328,245 A | 5/1982 | Yu et al. | |
| 4,358,603 A | 11/1982 | Yu | |
| 4,364,923 A | 12/1982 | Cook et al. | |
| 4,409,239 A | 10/1983 | Yu | |
| 4,410,545 A | 10/1983 | Yu et al. | |
| 4,414,209 A | 11/1983 | Cook et al. | |
| 4,617,415 A * | 10/1986 | Balthazor et al. ........... 558/169 |
| 4,935,404 A * | 6/1990 | Hunter et al. .................. 514/7 |
| 5,033,252 A | 7/1991 | Carter | |
| 5,052,558 A | 10/1991 | Carter | |
| 5,323,907 A | 6/1994 | Kalvelage | |
| 6,232,467 B1 | 5/2001 | Petasis et al. | |
| 6,602,817 B1 | 8/2003 | Petasis | |

OTHER PUBLICATIONS

Murray et al., 1993, CAS:119:180664.*
Duncan et al., 2002, CAS: 137:274431.*
Jomaaet et al., 2001, CAS: 136: 37770.*
Hubert et al., 1999, CAS: 132:108014.*
Spengler et al., 1998, CAS: 129:189654.*
Knowles et al., 1995, CAS: 122:208344.*
Jezowska-Bojczuk et al., 1994, CAS: 120:281638.*
Balthazor et al., 1987, CAS: 106:50457.*
Issleib et al., 1981, CAS: 94:192407.*
(8) Sommer et al., 1980, CAS: 93:18656.*
Szabo, C. M. et al, "Inhibition of Geranylgeranyl Diphosphate Synthase by Bisphosphonates and Diphosphates: A Potential Route to new Bone Antiresportion and Antiparasitic Agents", Journal of Medicinal Chemistry, vol. 45, Issue 11, May 23, 2002, pp. 2185-2196.
Morty, R.E. et al., "Characterization of the Antitrypanosomal Activity of Peptidyl α-Aminoalkyl Phosphonate Diphenyl Esters", Biochemical Pharmacology, vol. 60, Issue 10, Nov. 15, 2000, pp. 1497-1504.
Rodan, G. et al., "Therapeutic Approaches to Bone Diseases", Science, vol. 289, Issue 5484, Sep. 1, 2000, pp. 1508-1514.
Petasis, N. et al., "A New and Practical Synthesis of α-Amino Acids from Alkenyl Acids", Journal of the American Chemical Society, vol. 119, Issue 2; Jan. 15, 1997, pp. 445-446.
Petasis, N. A. et al., "A New Synthesis of α-Arylglycines from Aryl Boronic Acids", Tetrahedron, vol. 53, Issue 48, Dec. 1, 1997, pp. 16463-16470.
Petasis, N. A. et al, "Highly Stereocontrolled One-Step Synthesis of anti-β-Amino Alcohols from Organoboronic Acids, Amines, and α-Hydroxy Aldehydes", Journal of the American Chemical Society, vol. 120, Issue 45, Nov. 18, 1998, pp. 11798-11799.
Prakash, G. K. Surya et al., "Stereoselective Synthesis of anti-α-(Difluoromethyl)-β-amino Alcohols by Boronic Acid Based Three-Component Condensation. Stereoselective Preparation of (2S,3R)-Difluorothreonine", Journal of Organic Chemistry, vol. 67, Issue 11, May 31, 2002, pp. 3718-3723.
Petasis, N. A. et al., "Synthesis of prperazinones and benzopiperazinones from 1,2-diamines and organoboronic acids", Tetrahedron Letters, vol. 41, Issue 49, Dec. 2, 2000, pp. 9607-9611.

* cited by examiner

*Primary Examiner*—Rei-Tsang Shiao
(74) *Attorney, Agent, or Firm*—Fish & Richardson P.C.

(57) ABSTRACT

Aminophosphonate and amino bisphosphonate compounds and methods for their preparation are provided. Also provided are pharmaceutical and agricultural compositions containing the compounds. The compounds and compositions are useful in methods for treatment of various diseases, including, inflammation, autoimmune disease, cardiovascular disease, bacterial infection, viral disease, abnormal cell proliferation, bone resorption disease, osteoporosis, or parasitic disease and in various agricultural methods, including, methods of eradicating weeds.

66 Claims, No Drawings

AMINO PHOSPHONATE AND AMINO BIS-PHOSPHONATE DERIVATIVES

RELATED APPLICATIONS

Benefit of priority under 35 U.S.C. §119(e) to U.S. provisional application Ser. No. 60/501,937, filed Sep. 10, 2003, to Petasis et al., entitled "AMINO PHOSPHONATE AND AMINO BISPHOSPHONATE DERIVATIVES" is claimed. The subject matter of the above-referenced application is incorporated by reference in its entirety.

STATEMENT REGARDING FEDERALLY SPONSORED RESEARCH

The U.S. Government may have certain rights in this invention pursuant to Grant No. GM 45970 awarded by the National Institutes of Health.

FIELD OF THE INVENTION

Compounds, compositions and methods using amino phosphonates for treating a variety of disorders, such as, proliferative diseases, autoimmune diseases, infectious diseases, cardiovascular diseases and inflammatory diseases, are provided.

BACKGROUND OF THE INVENTION

Provided herein are amino phosphonates and amino bis-phosphonates. Also provided are methods for the preparation and use of such compounds and their structural analogs. The present invention relates to amino phosphonates of general formula 1-3 and amino bis-phosphonates of general formula 4.

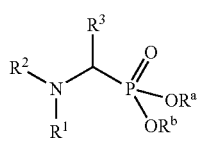

1

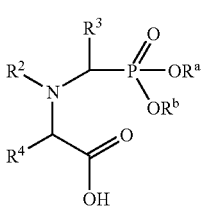

2

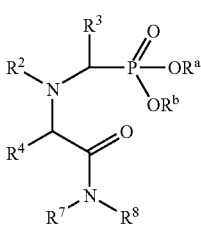

3

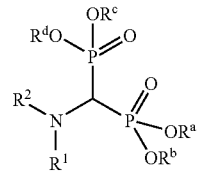

4

Amino phosphonates of general formula 1 have long been used as surrogates for amino acids in a variety of enzyme inhibitors and have been used in a number of applications in the pharmaceutical and agrochemical industries. Amino phosphonates of general formula 2 or 3, have been used extensively as inhibitors of proteases and other enzymes ((a) Mader, M. M.; Bartlett, P. A. Chem. Rev. 1997, 97, 1281. (b) Powers, J. C.; Asgian, J. L.; Ekici, O. D.; James, K. E. Chem. Rev. 2002, 102, 4639. (c) De Lombaert, S. et al. Bioorg. Med. Chem. Lett. 1995, 5, 151. (d) De Lombaert, S. et al. J. Med. Chem. 2000, 43, 488. (e) Bird, J. et al. Bioorg. Med. Chem. Lett. 1995, 5, 2593. (f) Ding, J.; Fraser, M. E.: Bartlett, P. A: Am. Chem. Soc., 1998, 120, 4610) and have exhibited a range of useful activities as pharmaceuticals and agrochemicals (Quin, L. D. A Guide to Organophosphorus Chemistry; Wiley-Interscience: New York, 2000) For example, amino phosphonates have served as key structural components of antiviral agents, antitrypanosomal agents, antibacterial agents and anticancer agents. Amino phosphonates have also been used as agrochemicals and as chelating agents or surfactants in industrial applications Amino bis-phosphonates of general formula 4 have been used as diphosphate mimics for the treatment of bone resorption diseases, and as antiparasitic agents ((a) Szabo, C. M. etal J. Med. Chem. 2002, 45, 2185. (b) Morty, R. E. etal. Biochemical Pharmacology, 2000, 60, 1497. (c) Rodan, G. A.: Martin, T. J. Science 2000, 289, 1508).

The present invention also provides a process for the synthesis of functionalized amino phosphonates and amino bis-phosphonates via the one-step three-component reaction among an amine derivative, a carbonyl derivative and an organoboron compound. This process is related to the previously reported general method for the synthesis of amine derivatives, including amino acids and amino alcohols. ((a) Petasis, N. A.; Zavialov, I. A., 2001, U.S. Pat. No. 6,232,467. (b) Petasis, N. A. 2003, U.S. Pat. No. 6,602,817 B1. (c) Petasis, N. A.; Zavialov, I. A., J. Am. Chem. Soc., 1997, 119, 445. (d) Petasis, N. A.; Goodman, A.; Zavialov, I. A. Tetrahedron, 1997, 53, 16463. (e) Petasis, N. A.; Zavialov, I. A., J. Am. Chem. Soc., 1998, 120, 11798. (f) Prakash G. K. S.; Mandal M.; Schweizer, S.; Petasis, N. A.; Olah, G. A. J. Org. Chem., 2002, 67, 3718. (g) Petasis, N. A.; Patel, Z. D., Tet. Lett, 2000, 41, 9607).

SUMMARY OF THE INVENTION

Provided herein are substituted amino phosphonates of the general formula 5:

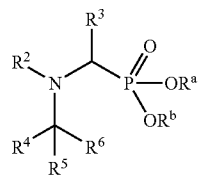

5 wherein:
$R^2$ is hydrogen, alkyl, allyl, aryl, heteroaryl, acyl, sulfonyl, amino, alkylamino, dialkylamino, acylamino, sulfonylamino, and alkoxy;
$R^3$ is hydrogen, alkyl, alkenyl, aryl, heteroaryl, phosphonic acid, phosphonate or phosphonamido;
$R^4$ is alkyl, aryl, heteroaryl, allyl, alkenyl, alkynyl, or allenyl;
$R^5$ and $R^6$ independently selected from a group consisting of: hydrogen, alkyl, hydroxyalkyl, polyhydroxyalkyl, aryl, heteroaryl, alkenyl, alkynyl, allenyl, formyl, acyl, aminoacyl, carboxy or alkoxyacyl;
$R^a$—$R^d$ are independently selected from a group consisting of: hydrogen, alkyl, aryl, heteroaryl, ammonium, tetraalkyl ammonium or a metal cation, provided that $R^a$—$R^d$ can also be joined together forming a ring In one embodiment the invention provides new substituted amino bis-phosphonates of the general formula 6:

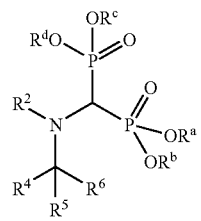

6 wherein:
$R^2$ is hydrogen, alkyl, allyl, aryl, heteroaryl, acyl, sulfonyl, amino, alkylamino, dialkylamino, acylamino, sulfonylamino, and alkoxy;
$R^4$ is alkyl, aryl, heteroaryl, allyl, alkenyl, alkynyl, or allenyl;
$R^5$ and $R^6$ independently selected from a group consisting of: hydrogen, alkyl, hydroxyalkyl, polyhydroxyalkyl, aryl, heteroaryl, alkenyl, alkynyl, allenyl, formyl, acyl, aminoacyl, carboxy or alkoxyacyl;
$R^a$—$R^d$ are independently selected from a group consisting of: hydrogen, alkyl, aryl, heteroaryl, ammonium, tetraalkyl ammonium or a metal cation, provided that $R^a$—$R^d$ can also be joined together forming a ring In some embodiments the invention provides compounds having a general formula selected from a group consisting of 7-12:

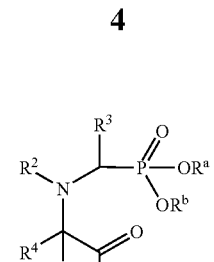

7

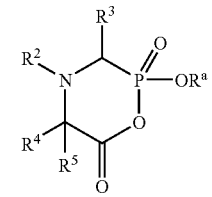

8

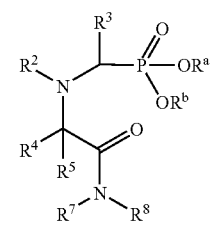

9

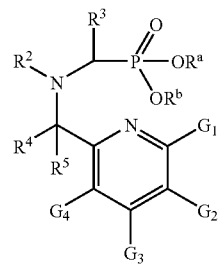

10

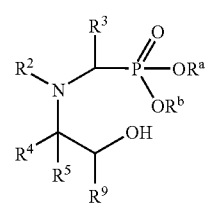

11

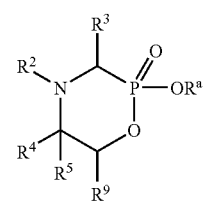

12 wherein:
$R^2$ is hydrogen, alkyl, allyl, aryl, heteroaryl, acyl, sulfonyl, amino, alkylamino, dialkylamino, acylamino, sulfonylamino, and alkoxy;
$R^3$ is hydrogen, alkyl, alkenyl, aryl, heteroaryl, phosphonic acid, phosphonate or phosphonamido;
$R^4$ is alkyl, aryl, heteroaryl, allyl, alkenyl, alkynyl, or allenyl;
$R^5$ and $R^6$ independently selected from a group consisting of: hydrogen, alkyl, hydroxyalkyl, polyhydroxyalkyl, aryl, heteroaryl, alkenyl, alkynyl, allenyl, formyl, acyl, aminoacyl, carboxy or alkoxyacyl;

$R^7$ and $R^8$ are independently selected from a group consisting of hydrogen, alkyl, allyl, aryl, heteroaryl, hydroxyl, alkoxy, aryloxy, acyl, sulfonyl, amino, alkylamino, dialkylamino, acylamino, sulfonylamino, and alkoxy, provided that $R^7$ and $R^8$ can also be connected together forming a ring;

$R^9$ is hydrogen, alkyl, aryl, heteroaryl, alkenyl, alkynyl, allenyl, hydroxyalkyl, or polyhydroxyalkyl;

$R^a$—$R^b$ are independently selected from a group consisting of hydrogen, alkyl, aryl, heteroaryl, ammonium, tetraalkyl ammonium or a metal cation, provided that $R^a$—$R^d$ can also be joined together forming a ring.

$G^1$-$G^4$ are independently selected from a group consisting of hydrogen, alkyl, aryl, heteroaryl, hydroxyl, alkoxy, aryloxy, chloro, bromo, fluoro, dialkylamino, acylamino, sulfonylamino, and provided that $G^1$-$G^4$ can also be connected together forming a ring.

The invention also features a method for the preparation of substituted amino phosphonates of general formula 5 from the reaction among an amino phosphonate 13 with a carbonyl compound 14 and an organoboron derivative 15 or 16 in the presence or absence of a Lewis acid

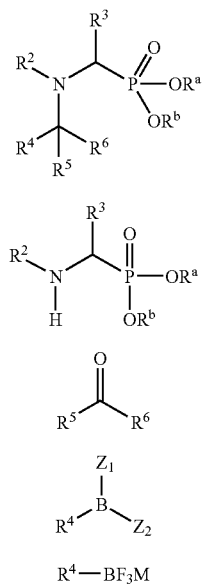

wherein:

$R^2$ is hydrogen, alkyl, allyl, aryl, heteroaryl, acyl, sulfonyl, amino, alkylamino, dialkylamino, acylamino, sulfonylamino, and alkoxy;

$R^3$ is hydrogen, alkyl, alkenyl, aryl, heteroaryl, phosphonic acid, phosphonate or phosphonamido;

$R^4$ is alkyl, aryl, heteroaryl, allyl, alkenyl, alkynyl, or allenyl;

$R^5$ and $R^6$ independently selected from a group consisting of: hydrogen, alkyl, hydroxyalkyl, polyhydroxyalkyl, aryl, heteroaryl, alkenyl, alkynyl, allenyl, formyl, acyl, aminoacyl, carboxy or alkoxyacyl;

$R^a$—$R^d$ are independently selected from a group consisting of: hydrogen, alkyl, aryl, heteroaryl, ammonium, tetraalkyl ammonium or a metal cation, provided that $R^a$—$R^d$ can also be joined together forming a ring;

$Z^1$ and $Z^2$ are independently selected from a group consisting of hydroxyl, alkoxy, aryloxy, amino and sulfonylamino, provided that $Z^1$ and $Z^2$ can also be joined together forming a ring;

M is a cation selected from a group consisting of the cations of: potassium, sodium, lithium, cesium, magnesium, ammonium, tetraalkyl ammonium or aryl-alkyl ammonium.

In particular embodiments, compounds 13-15 can also be connected to a polymeric chain or other solid phase material.

The invention also provides pharmaceutical compositions containing compounds of general formulae 5-12 and methods of their use.

DETAILED DESCRIPTION OF THE INVENTION

A. Definitions

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

As used herein, the nomenclature alkyl, alkoxy, carbonyl, etc. is used as is generally understood by those of skill in this art.

As used in this specification, alkyl groups can include straight-chained, branched and cyclic alkyl radicals containing up to about 20 carbons, or 1 to 16 carbons, and are straight or branched. Exemplary alkyl groups herein include, but are not limited to, methyl, ethyl, propyl, isopropyl, isobutyl, n-butyl, sec-butyl, tert-butyl, isopentyl, neopentyl, tert-pentyl and isohexyl. As used herein, lower alkyl refer to carbon chains having from about 1 or about 2 carbons up to about 6 carbons. Suitable alkyl groups may be saturated or unsaturated. Further, an alkyl may also be substituted one or more times on one or more carbons with substituents selected from a group consisting of C1-C15 alkyl, allyl, allenyl, alkenyl, C3-C7 heterocycle, aryl, halo, hydroxy, amino, cyano, oxo, thio, alkoxy, formyl, carboxy, carboxamido, phosphoryl, phosphonate, phosphonamido, sulfonyl, alkylsulfonate, arylsulfonate, and sulfonamide. Additionally, an alkyl group may contain up to 10 heteroatoms, in certain embodiments, 1, 2, 3, 4, 5, 6, 7, 8 or 9 heteroatom substituents. Suitable heteroatoms include nitrogen, oxygen, sulfur and phosphorous.

As used herein, "cycloalkyl" refers to a mono- or multicyclic ring system, in certain embodiments of 3 to 10 carbon atoms, in other embodiments of 3 to 6 carbon atoms. The ring systems of the cycloalkyl group may be composed of one ring or two or more rings which may be joined together in a fused, bridged or spiro-connected fashion.

As used herein, "aryl" refers to aromatic monocyclic or multicyclic groups containing from 3 to 16 carbon atoms. As used in this specification, aryl groups are aryl radicals which may contain up to 10 heteroatoms, in certain embodiments, 1, 2, 3 or 4 heteroatoms. An aryl group may also be optionally substituted one or more times, in certain embodiments, 1 to 3 or 4 times with an aryl group or a lower alkyl group and it may be also fused to other aryl or cycloalkyl rings. Suitable aryl groups include, for example, phenyl, naphthyl, tolyl, imidazolyl, pyridyl, pyrroyl, thienyl, pyrimidyl, thiazolyl and furyl groups.

As used in this specification, a ring is defined as having up to 20 atoms that may include one or more nitrogen, oxygen, sulfur or phosphorous atoms, provided that the ring can have one or more substituents selected from the group consisting of hydrogen, alkyl, allyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, phosphonate, phosphonamido, and sulfonyl, and further provided that the ring may also contain one or more fused rings, including carbocyclic, heterocyclic, aryl or heteroaryl rings.

As used herein, alkenyl and alkynyl carbon chains, if not specified, contain from 2 to 20 carbons, or 2 to 16 carbons, and are straight or branched. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrrolidinyl, pyrimidinyl, tetrazolyl, thienyl, pyridyl, pyrrolyl, N-methylpyrrolyl, quinolinyl and isoquinolinyl.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "aralkyl" refers to an alkyl group in which one of the hydrogen atoms of the alkyl is replaced by an aryl group.

As used herein, "halo", "halogen" or "halide" refers to F, Cl, Br or I.

As used herein, "haloalkyl" refers to an alkyl group in which one or more of the hydrogen atoms are replaced by halogen. Such groups include, but are not limited to, chloromethyl and trifluoromethyl.

As used herein, "alkoxy" refers to RO—, in which R is alkyl, including lower alkyl.

As used herein, "aryloxy" refers to RO—, in which R is aryl, including lower aryl, such as phenyl.

As used herein "subject" is an animal, typically a mammal, including human, such as a patient.

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamineand other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl ar heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl ar heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, treatment means any manner in which one or more of the symptoms of a disease or disorder are ameliorated or otherwise beneficially altered. Treatment also encompasses any pharmaceutical use of the compositions herein, such as use for treating a cancer.

As used herein, amelioration of the symptoms of a particular disorder by administration of a particular compound or pharmaceutical composition refers to any lessening, whether permanent or temporary, lasting or transient that can be attributed to or associated with administration of the composition.

The term "combinatorial library" as used herein refers to a collection of compounds that are made by the same process, by varying one or more of the reagents. Combinatorial libraries may be made as mixtures of compounds, or as individual pure compounds, generally depending on the methods used for identifying active compounds. Where the active compound may be easily identified and distinguished from other compounds present by physical and/or chemical characteristics, it may be preferred to provide the library as a large mixture of compounds. Large combinatorial libraries may also be prepared by massively parallel synthesis of individual compounds, in which case compounds are typically identified by their position within an array. Intermediate between these two strategies is "deconvolution", in which the library is prepared as a set of sub-pools, each having a known element and a random element. For example, using the process of the invention each sub-pool might be prepared from only a single amine (where each sub-pool contains a different amine), but a mixture of different carbonyl derivatives (or organoboron reagents). When a sub-pool is identified as having activity, it is resynthesized as a set of individual compounds (each compound having been present in the original active sub-pool), and tested again to identify the compounds responsible for the activity of the sub-pool.

As used herein, herbicide is a pesticide used to kill unwanted plants while leaving the desired crop relatively unharmed.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

B. Compounds

Provided herein are substituted amino phosphonates of the general formula 5:

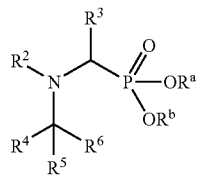

5 wherein:
- $R^2$ is hydrogen, alkyl, allyl, aryl, heteroaryl, acyl, sulfonyl, amino, alkylamino, dialkylamino, acylamino, sulfonylamino, and alkoxy;
- $R^3$ is hydrogen, alkyl, alkenyl, aryl, heteroaryl, phosphonic acid, phosphonate or phosphonamido;
- $R^4$ is alkyl, aryl, heteroaryl, allyl, alkenyl, alkynyl, or allenyl;
- $R^5$ and $R^6$ independently selected from a group consisting of: hydrogen, alkyl, hydroxyalkyl, polyhydroxyalkyl, aryl, heteroaryl, alkenyl, alkynyl, allenyl, formyl, acyl, aminoacyl, carboxy or alkoxyacyl;
- $R^a$—$R^d$ are independently selected from a group consisting of: hydrogen, alkyl, aryl, heteroaryl, ammonium, tetraalkyl ammonium or a metal cation, provided that $R^a$—$R^d$ can also be joined together forming a ring.

In one embodiment the invention provides new substituted amino bis-phosphonates of the general formula 6:

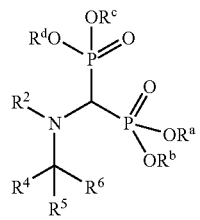

6 wherein:
- $R^2$ is hydrogen, alkyl, allyl, aryl, heteroaryl, acyl, sulfonyl, amino, alkylamino, dialkylamino, acylamino, sulfonylamino, and alkoxy;
- $R^4$ is alkyl, aryl, heteroaryl, allyl, alkenyl, alkynyl, or allenyl;
- $R^5$ and $R^6$ independently selected from a group consisting of: hydrogen, alkyl, hydroxyalkyl, polyhydroxyalkyl, aryl, heteroaryl, alkenyl, alkynyl, allenyl, formyl, acyl, aminoacyl, carboxy or alkoxyacyl;
- $R^a$—$R^d$ are independently selected from a group consisting of: hydrogen, alkyl, aryl, heteroaryl, ammonium, tetraalkyl ammonium or a metal cation, provided that $R^a$—$R^d$ can also be joined together forming a ring.

In some embodiments the invention provides compounds having a general formula selected from a group consisting of 7-12:

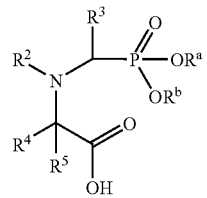

7

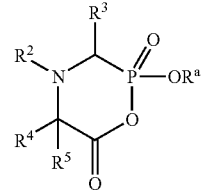

8

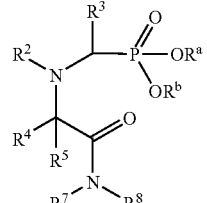

9

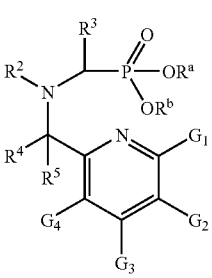

10

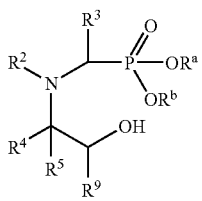

11

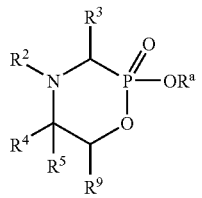

12 wherein:
- $R^2$ is hydrogen, alkyl, allyl, aryl, heteroaryl, acyl, sulfonyl, amino, alkylamino, dialkylamino, acylamino, sulfonylamino, and alkoxy;
- $R^3$ is hydrogen, alkyl, alkenyl, aryl, heteroaryl, phosphonic acid, phosphonate or phosphonamido;
- $R^4$ is alkyl, aryl, heteroaryl, allyl, alkenyl, alkynyl, or allenyl;

$R^5$ and $R^6$ independently selected from a group consisting of: hydrogen, alkyl, hydroxyalkyl, polyhydroxyalkyl, aryl, heteroaryl, alkenyl, alkynyl, allenyl, formyl, acyl, aminoacyl, carboxy or alkoxyacyl;

$R^7$ and $R^8$ are independently selected from a group consisting of hydrogen, alkyl, allyl, aryl, heteroaryl, hydroxyl, alkoxy, aryloxy, acyl, sulfonyl, amino, alkylamino, dialkylamino, acylamino, sulfonylamino, and alkoxy, provided that $R^7$ and $R^8$ can also be connected together forming a ring;

$R^9$ is hydrogen, alkyl, aryl, heteroaryl, alkenyl, alkynyl, allenyl, hydroxyalkyl, or polyhydroxyalkyl;

$R^a$—$R^d$ are independently selected from a group consisting of hydrogen, alkyl, aryl, heteroaryl, ammonium, tetraalkyl ammonium or a metal cation, provided that $R^a$—$R^d$ can also be joined together forming a ring;

$G^1$-$G^4$ are independently selected from a group consisting of hydrogen, alkyl, aryl, heteroaryl, hydroxyl, alkoxy, aryloxy, chloro, bromo, fluoro, dialkylamino, acylamino, sulfonylamino, and provided that $G^1$-$G^4$ can also be connected together forming a ring.

Some examples of compounds provided herein only for the purpose of illustration, are compounds of formulae 17-36.

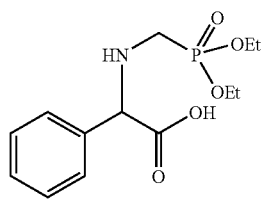

17

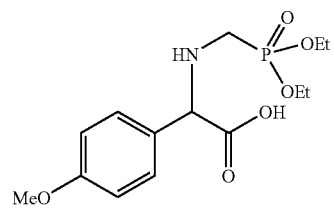

18

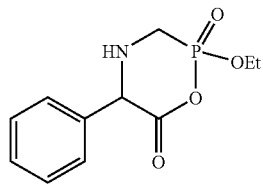

19

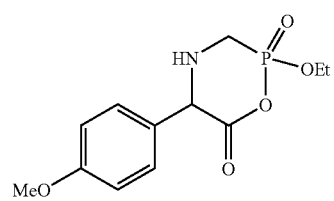

20

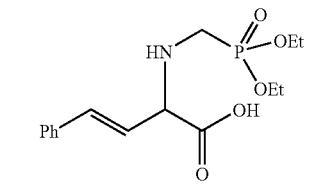

21

-continued

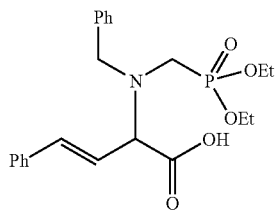

22

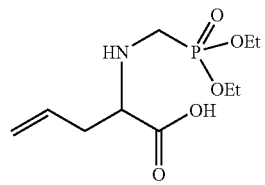

23

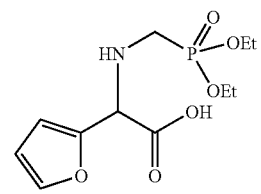

24

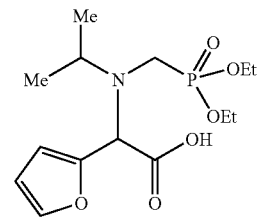

25

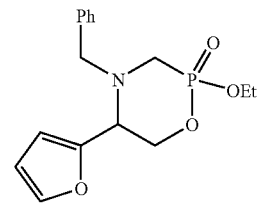

26

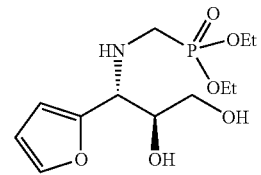

27

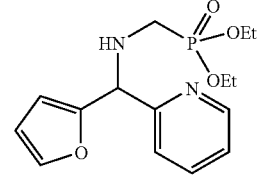

28

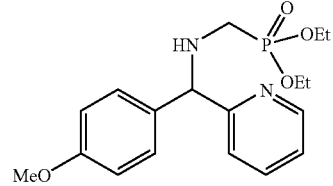

29

-continued

30
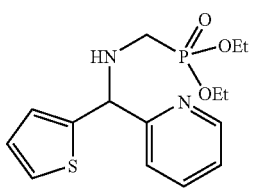

31
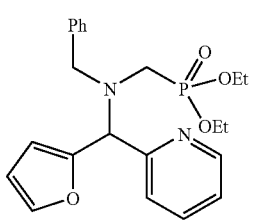

32
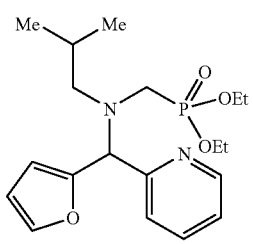

33
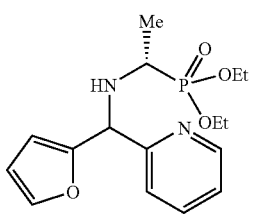

34
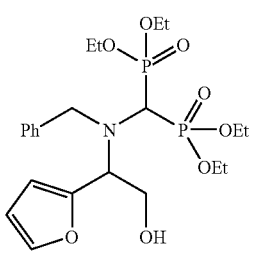

35
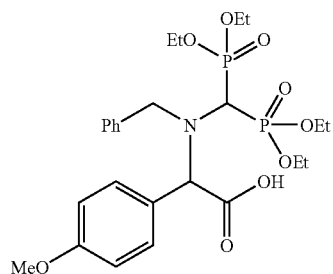

-continued

5
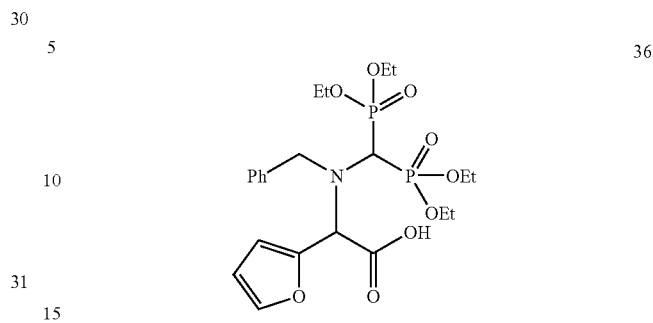
36

C. Preparation of the Compounds

The amino phosphonate or amino bis-phosphonate compounds provided herein are prepared as described herein. In certain embodiments, the amino phosphonate or an amino bis-phosphonate compound of the general formula 5 can be prepared according to Scheme 1. Substituted amino phosphonates of general formula 5 can be prepared from the reaction among an amino phosphonate 13 with a carbonyl compound 14 and an organoboron derivative 15 or 16 in the presence or absence of a Lewis acid Scheme 1
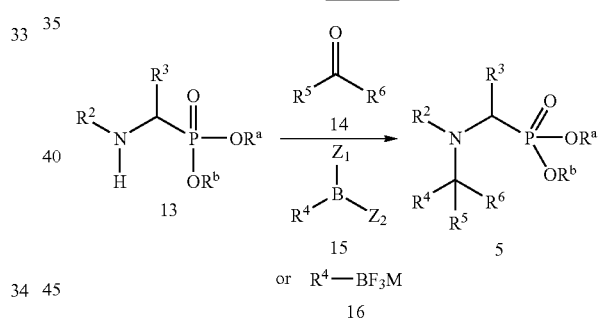

wherein:
R$^2$ is hydrogen, alkyl, allyl, aryl, heteroaryl, acyl, sulfonyl, amino, alkylamino, dialkylamino, acylamino, sulfonylamino, and alkoxy;

R$^3$ is hydrogen, alkyl, alkenyl, aryl, heteroaryl, phosphonic acid, phosphonate or phosphonamido;

R$^4$ is alkyl, aryl, heteroaryl, allyl, alkenyl, alkynyl, or allenyl;

R$^5$ and R$^6$ independently selected from a group consisting of: hydrogen, alkyl, hydroxyalkyl, polyhydroxyalkyl, aryl, heteroaryl, alkenyl, alkynyl, allenyl, formyl, acyl, aminoacyl, carboxy or alkoxyacyl;

R$^a$—R$^d$ are independently selected from a group consisting of: hydrogen, alkyl, aryl, heteroaryl, ammonium, tetraalkyl ammonium or a metal cation, provided that R$^a$—R$^d$ can also be joined together forming a ring;

$Z^1$ and $Z^2$ are independently selected from a group consisting of hydroxyl, alkoxy, aryloxy, amino and sulfonylamino, provided that $Z^1$ and $Z^2$ can also be joined together forming a ring;

M is a cation selected from a group consisting of the cations of: potassium, sodium, lithium, cesium, magnesium, ammonium, tetraalkyl ammonium or aryl-alkyl ammonium.

Other compounds provided herein can be prepared similarly.

The provided process is efficient at room temperature in a solvent such as acetonitrile and is experimentally simple. A number of boronic acid derivatives as well as amino phosphonates, both primary and secondary, work well in this process. The required amino phosphonates can be readily prepared by methods known in the art (Quin, L. D. A Guide to Organophosphorus Chemistry; Wiley-Interscience: New York, 2000). In addition to boronic acids, the process can include the use of trifluoroborate salts either directly or in the presence of a Lewis acid.

This process is also readily adaptable to solid phase or parallel synthesis and the synthesis of combinatorial libraries. For example, a combinatorial library can be prepared by combining a selected group of boronic acids with a selected group of amino phosphonates or amino bis-phosphonates and a group of carbonyl compounds.

In certain embodiments, compounds 13-15 can also be connected to a polymeric chain or other solid phase material.

Some examples of the process provided with the present invention given only for the purpose of illustration, are shown in Schemes 2-4.

-continued

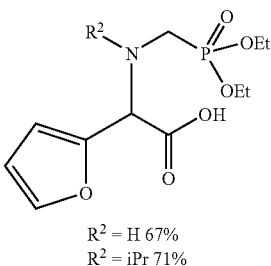

$R^2$ = H 67%
$R^2$ = iPr 71%

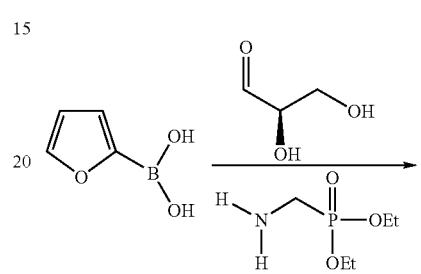

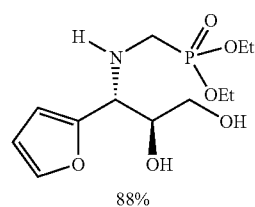

88%

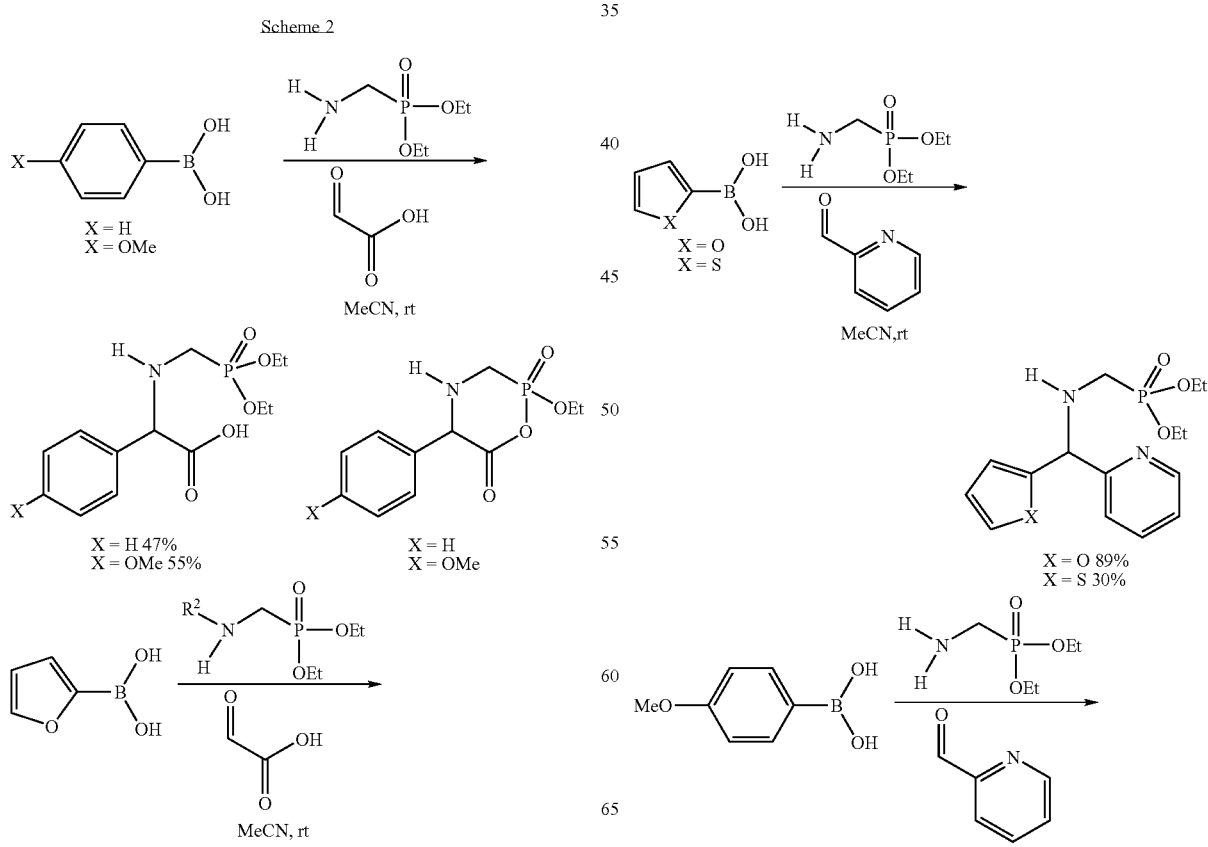

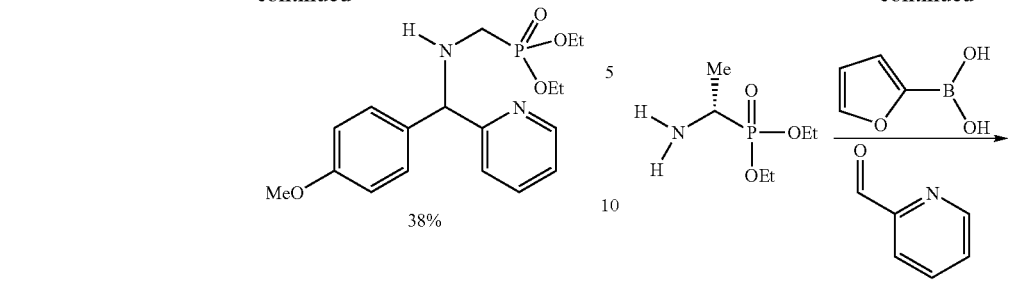
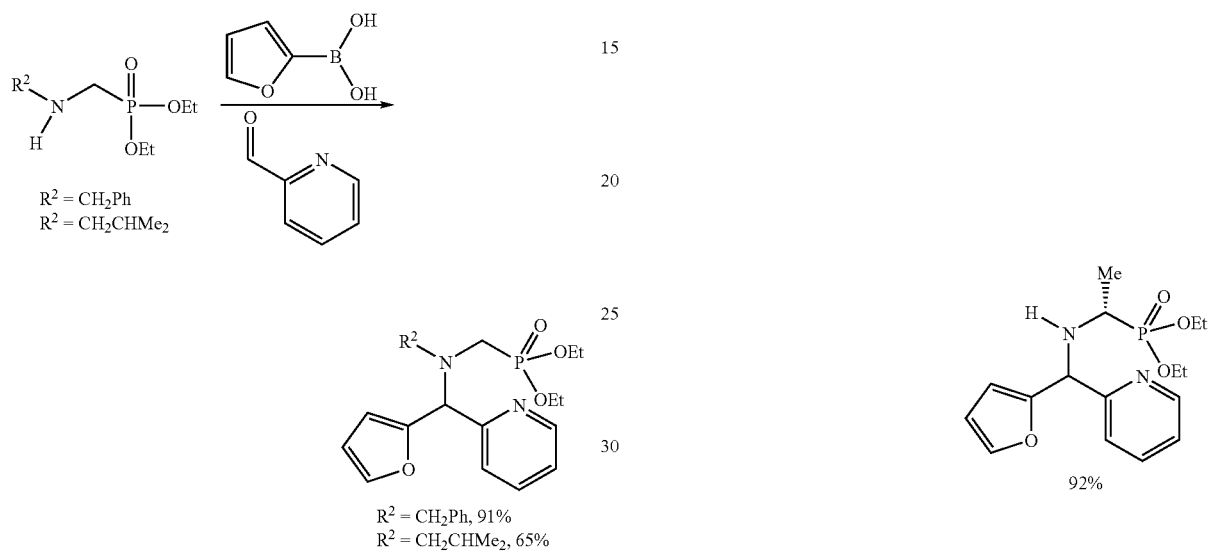
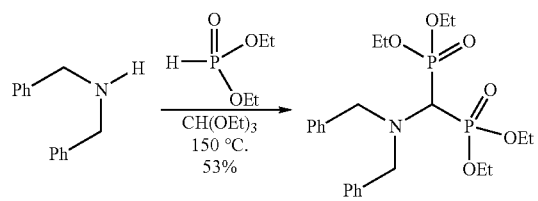
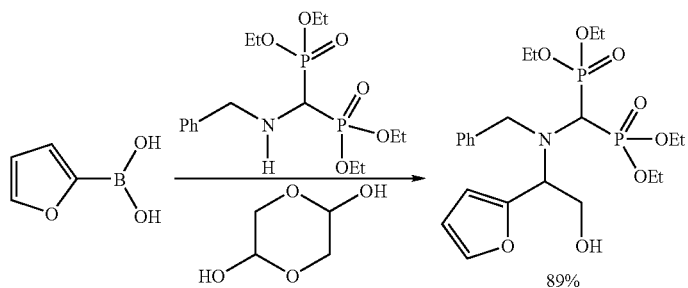

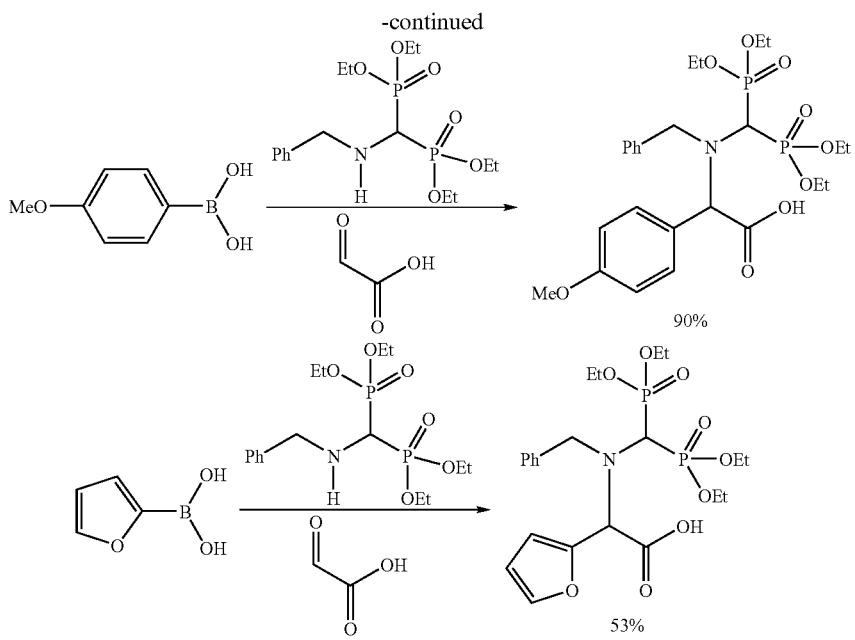

D. Formulation of Pharmaceutical Compositions

The pharmaceutical compositions provided herein contain therapeutically effective amounts of one or more of compounds provided herein in a pharmaceutically acceptable carrier.

The compositions contain one or more compounds provided herein. The compounds are preferably formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art (see, e.g., Ansel Introduction to Pharmaceutical Dosage Forms, Fourth Edition 1985, 126).

In the compositions, effective concentrations of one or more compounds or pharmaceutically acceptable derivatives is (are) mixed with a suitable pharmaceutical carrier or vehicle. The compounds may be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that treats, prevents, or ameliorates one or more of the symptoms of conditions including, but not limited to, undesired cell proliferation, coronary restenosis, osteoporosis and syndromes characterized by chronic inflammation, autoimmune diseases and cardiovascular diseases.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated undesired cell proliferation, coronary restenosis, osteoporosis, syndromes characterized by chronic inflammation, autoimmune diseases and-cardiovascular diseases as described herein.

Typically a therapeutically effective dosage should produce a serum concentration of active ingredient of from about 0.1 ng/ml to about 50-100 µg/ml. The pharmaceutical compositions typically should provide a dosage of from about 0.001 mg to about 2000 mg of compound per kilogram of body weight per day. Pharmaceutical dosage unit forms are prepared to provide from about 1 mg to about 1000 mg and preferably from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing diseases or disorders associated with undesired cell proliferation, coronary restenosis, osteoporosis, syndromes characterized by chronic inflammation, autoimmune diseases and cardiovascular diseases as described herein. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including orally, parenterally, rectally, topically and locally. For oral administration, capsules and tablets are presently preferred. The compositions are in liquid, semi-liquid or solid form and are formulated in a manner suitable for each route of administration. Preferred modes of administration include parenteral and oral modes of administration. Oral administration is presently most preferred.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can contain along with the active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount sufficient to alleviate the symptoms of the treated subject.

Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain 0.001%-100% active ingredient, preferably 0.1-85%, typically 75-95%.

The active compounds or pharmaceutically acceptable derivatives may be prepared with carriers that protect the compound against rapid elimination from the body, such as time release formulations or coatings.

The compositions may include other active compounds to obtain desired combinations of properties. The compounds provided herein, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove, such as diseases or disorders associated with undesired cell proliferation, coronary restenosis, osteoporosis, syndromes characterized by chronic inflammation, autoimmune diseases and cardiovascular diseases. It is to be understood that such combination therapy constitutes a further aspect of the compositions and methods of treatment provided herein.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, preferably capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, 'suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl)acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, preferably more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a, more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage (10-1000 mg, preferably 100-500 mg) or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, preferably 5-35 mg, more preferably about 9-30 mg of lyophilized powder, is added per mL of sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, is 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

6. Articles of Manufacture

The compounds or pharmaceutically acceptable derivatives thereof can be packaged as articles of manufacture containing packaging material, a compound or pharmaceutically acceptable derivative thereof provided herein, which is used for treatment, prevention or amelioration of one or more symptoms associated with undesired cell proliferation, coronary restenosis, osteoporosis, syndromes characterized by chronic inflammation, autoimmune diseases and cardiovascular diseases condition, and a label that indicates that the compound or pharmaceutically acceptable derivative thereof is used for treatment, prevention or amelioration of one or more symptoms associated with undesired cell proliferation, coronary restenosis, osteoporosis, syndromes characterized by chronic inflammation, autoimmune diseases and cardiovascular diseases.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disorder associated with undesired cell proliferation, coronary restenosis, osteoporosis, syndromes characterized by chronic inflammation, autoimmune diseases and cardiovascular diseases condition.

E. Methods of use of the Compounds and Compositions

The compounds of the invention are structural analogs of naturally-occurring molecules that are known to have biological activity against a wide variety of targets, including diseases or conditions associated with undesired cell proliferation, coronary restenosis, osteoporosis, syndromes characterized by chronic inflammation, autoimmune diseases and cardiovascular diseases. As such, the compounds provided herein are expected to have similar activity against those targets.

Accordingly, in one embodiment, methods of ameliorating or treating diseases or conditions associated with inflammation or inflammatory response and/or autoimmune diseases, involving the administration to a subject of a therapeutically effective amount of a compound or compounds of the invention, such that inflammation or an inflammatory response and/or autoimmune diseases are significantly reduced or eliminated in the subject. A significant reduction includes the reduction or elimination of a symptom or symptoms associated with the inflammation or inflammatory response and/or autoimmune diseases.

Examples of chronic inflammation and/or autoimmune diseases include but are not limited to rheumatoid arthritis and other forms of arthritis, asthma, psoriasis, inflammatory bowel- disease, systemic lupus erythematosus, systemic dermatomyositis, inflammatory ophthalmic diseases, autoimmune hematologic disorders, multiple sclerosis, vasculitis, idiopathic nephrotic syndrome, transplant rejection and graft versus host disease.

In another embodiment, methods of ameliorating or treating diseases or conditions associated with undesired cell proliferation, such as cancer, involving the administration to a subject of a therapeutically effective amount of a compound or a pharmaceutically acceptable derivative thereof. In general, an effective amount is an amount sufficient to ensure adequate exposure of a target cell population, such that abnormal cell proliferation is substantially slowed or halted. A target population is a population of cells undergoing abnormal cell proliferation, such as cancerous and/or tumorous growth.

Examples of cancers include, but are not limited to, non-small cell lung cancer, head and neck squamous cancers, colorectal cancer, prostate cancer, and breast cancer, acute lymphocytic leukemia, adult acute myeloid leukemia, adult non-Hodgkin's lymphoma, brain tumors, cervical cancers, childhood cancers, childhood sarcoma, chronic lymphocytic leukemia, chronic myeloid leukemia, esophageal cancer, hairy cell leukemia, kidney cancer, liver cancer, multiple myeloma, neuroblastoma, oral cancer, pancreatic cancer, primary central nervous system lymphoma, skin cancer, and small-cell lung cancer. Childhood cancers amenable to treatment by the methods and with the compositions provided herein include, but are not limited to, brain stem glioma, cerebellar astrocytoma, cerebral astrocytoma, ependymoma, Ewing's sarcoma and family of tumors, germ cell tumor, Hodgkin's disease, ALL, AML, liver cancer, medulloblastoma, neuroblastoma, non-Hodgkin's lymphoma, osteosarcoma, malignant fibrous histiocytoma of bone, retinoblastoma, rhabdomyosarcoma, soft tissue sarcoma, supratentorial primitive neuroectodermal and pineal tumors, unusual childhood cancers, visual pathway and hypothalamic glioma, Wilms' tumor, and other childhood kidney tumors.

In another embodiment, methods of ameliorating or treating cardiovascular diseases, such as arteriosclerosis, atherosclerosis, stroke, ischemia, endothelium dysfunctions, peripheral vascular disease, coronary heart disease, myocardial infarction, cerebral infarction or restenosis, involving the administration to a subject of a therapeutically effective amount of a compound or a pharmaceutically acceptable derivative thereof.

In one embodiment, the compounds provided herein can be used in agricultural applications, including, but not limited to, eradicating weeds by applying the compounds provided herein to a locus where weeds are growing or are likely to grow in an amount effective for eradicating the weeds.

The compounds will be further described in the following examples, which are illustrative only, and which are not intended to limit the scope of the subject matter described in the claims.

EXAMPLES

In the following examples, efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric. Starting materials used in these examples are generally either commercially available or can be readily prepared from commercially available reagents by a procedure involving one or more steps.

Example 1

2-((Diethoxyphosphoryl)methylamino)-2-(furan-2-yl)acetic acid

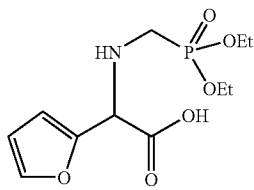

Diethyl aminomethylphosphonate, prepared according to literature (Davidsen, S. K.; Philips, G. W.; Martin, S. F. *Organic Synthesis CV* 8, 451.) (50 mg, 0.3 mmol), 2-furan boronic acid (67 mg, 0.6 mmol), glyoxylic acid monohydrate (28 mg, 0.3 mmol) was put into a 10ml round bottom flask, dissolved with 5 ml of acetonitrile. The mixture was stirred at room temperature for one day. Solvent was then removed and product was isolated by flash column chromatography using NH$_4$OH 5%, MeOH 20%, ethyl acetate 55%, dichloromethane 20% afforded 60 mg clear oil (67% yield). $^1$H NMR (360 MHz, CDCl$_3$) δ 1.23-1.33(td, J=7.3, 1.7 Hz, 6H), 2.86-2.98(d, J=13.3 Hz, 2H), 4.02-4.14(m, 4H), 4.49(s, 1H), 6.26-6.31(dd, J=3.2, 1.8 Hz, 1H), 6.31-6.36(d, J=3.2 Hz, 1H), 7.33-7.38(bs, 1H); $^{13}$C NMR (126 MHz, CDCl$_3$) δ 16.30(d, J=6 Hz), 41.51(d, J=156.5 Hz), 60.81(d, J=14.7 Hz), 62.40(t, J=6.8 Hz), 108.97, 110.27, 142.41, 151.19, 173.29.

Example 2

Diethyl ((4-methoxyphenyl)(pyridin-2-yl)methylamino)methylphosphonate

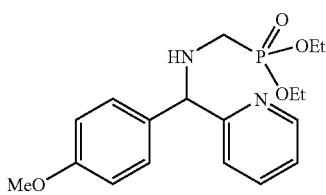

Prepared similarly to Example 1 (38% yield). $^1$H NMR (500 MHz, CDCl$_3$) δ 1.30-1.39(m, 6H), 2.93-3.00(d, J=13.3 Hz, 2H), 3.76-3.81(s, 3H), 4.10-4.22(m, 4H), 4.95-4.99(s, 1H), 6.84-6.89(d, J=8.9 Hz, 2H), 7.11-7.16(dd, J=4.8, 7.7 Hz, 1H), 7.27-7.33(d, J=8.2 Hz, 1H), 7.33-7.40(d, J=8.9 Hz, 2H), 7.58-7.64(t, J=7.6 Hz, 1H); 8.52-8.58(d, J=4.8 Hz, 1H); 1H); $^{13}$C NMR (126 MHz, CDCl$_3$) δ 16.44(d, J=5.9 Hz), 43.00(d, J=155.1 Hz), 55.30, 62.05(d, J=7.1 Hz), 68.35(d, J=17.3 Hz), 113.95, 121.62, 122.04, 128.91, 133.51, 136.60, 149.03, 159.00, 161.85.

Example 3

Diethyl (pyridin-2-yl(thiophen-2-yl)methylamino)methylphosphonate

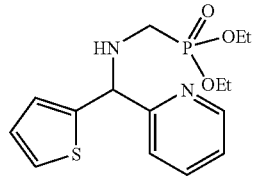

Prepared similarly to Example 1 (30% yield). $^1$H NMR (500 MHz, CDCl$_3$) δ 1.30-1.42(td, J=7.0, 4.2 Hz, 6H), 2.95-3.10(m, 2H), 4.12-4.25(m, 4H), 5.29(s, 1H), 6.93-6.97(dd, J=3.8, 5.2 Hz, 1H), 6.98-7.02(d, J=3.6 Hz, 1H), 7.16-7.22(dd, J=4.7, 7.5 Hz, 1H), 7.23-7.27(d, J=5.0 Hz, 1H), 7.33-7.40(d, J=8.2 Hz, 1H), 7.62-7.72(t, J=7.3 Hz, 1H), 8.55-8.62(d, J=4.6 Hz, 1H), $^{13}$C NMR (126 MHz, CDCl$_3$) δ 16.49(d, J=5.8 Hz), 43.01(d, J=155.6 Hz), 62.18(d, J=6.3 Hz), 62.30(d, J=6.8 Hz), 64.56(d, J=17.2 Hz), 121.87, 122.55, 125.73, 125.47, 126.58, 136.87, 145.66, 149.16, 160.70.

Example 4

Diethyl (benzyl(pyridin-2-yl(thiophen-2-yl)methyl)amino)methylphosphonate

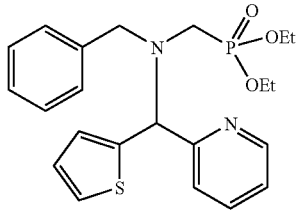

Prepared similarly to Example. 1 (91% yield). $^1$H NMR (360 MHz, CDCl$_3$) δ 1.21-1.33(dt, J=4.2, 7.0 Hz, 6H), 2.95-3.05(dd, J=7.1, 15.5 Hz, 1H), 3.11-3.23(dd, J=13.8, 15.7 Hz, 1H), 6.39-6.42(d, J=13.3 Hz, 1H), 3.98-4.12(m, 5H), 5.38(s, 1H), 6.35-6.39(dd, J=2.1, 3.5 Hz, 1H), 6.39-6.42(d, J=3.5 Hz, 1H), 7.13-7.19(m, 1H), 7.20-7.36(m, 3H), 7.40-7.46(m, 3H), 7.59-7.71(m, 2H), 8.53-8.59(d, J=4.8 Hz, 1H); $^{13}$C NMR (91 MHz, CDCl$_3$) δ 16.29(d, J=6.1 Hz), 46.05(d, J=163.7 Hz,), 56.38(d, J=6.6 Hz), 61.66(t, J=6.2 Hz), 63.04(d, J=10.1 Hz), 109.95, 110.52, 122.13, 123.42, 126.95, 128.13, 128.82, 136.25, 138.72, 142.26, 148.84, 152.07, 158.56.

Example 5

Diethyl (S)-1-(furan-2-yl(pyridin-2-yl)methylamino) ethylphosphonate

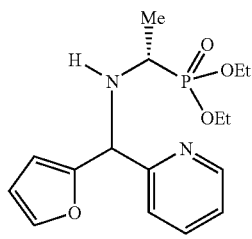

Prepared similarly to Example 1 (92% yield). $^1$H NMR (360 MHz, CDCl$_3$) δ 1.28-1.42(m, 9H), 3.92-3.06(m, 1H), 4.08-4.23(m, 4H), 5.36(s, 1H), 6.24-6.28(d, J=3.3 Hz, 1H), 6.29-6.34(dd, J=3.3, 2.0 Hz, 1H), 7.14-7.22(m, 1H), 7.35-7.37(d, J=2.0 Hz, 1H), 7.39-7.45(m, 1H), 7.64-7.68(t, J=7.2 Hz, 1H), 8.54-8.60(d, J=4.8 Hz, 1H); $^{13}$C NMR (90 MHz, CDCl$_3$) δ 15.49, 16.40(m), 47.66(d, J=150.7 Hz), 59.69, 54.11, 62.05, 107.51, 110.08, 122.04, 122.34, 136.54, 142.15, 148.97, 154.66, 159.33

Additional examples include the similar preparation of compounds of formula 17-36.

The above reactions can be performed in a variety of solvents, in certain embodiments, in acetonitrile as a solvent. The reactions are done either at room temperature or by heating up to 150° C. In certain embodiments, the reactions for preparing the compounds provided herein involve combining the amine, carbonyl and boron containing starting materials to form a reaction mixture, which directly produces the product in one-step.

It is understood that the foregoing detailed description and accompanying examples are merely illustrative, and are not to be taken as limitations upon the scope of the subject matter. Various changes and modifications to the disclosed embodiments will be apparent to those skilled in the art. Such changes and modifications, including without limitation those relating to the chemical structures, substituents, derivatives, intermediates, syntheses, formulations and/or methods of use provided herein, may be made without departing from the spirit and scope thereof. U.S. patents and publications referenced herein are incorporated by reference.

What is claimed is:

1. A compound of general formula:

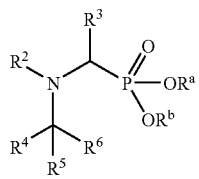

wherein:
R$^2$ is hydrogen, alkyl, allyl, aryl, acyl, sulfonyl, amino, alkylamino, dialkylamino, acylamino, sulfonylamino, or alkoxy;
R$^3$ is hydrogen, alkyl, alkenyl, aryl, phosphonic acid, phosphonate or phosphonamido;
R$^4$ is alkyl, aryl, furyl, thienyl, pyrrolyl, benzofuryl, benzothienyl, allyl, alkenyl, alkynyl, or allenyl;
R$^5$ is hydrogen, alkyl, or aryl;
R$^6$ is hydrogen, alkyl, hydroxyalkyl, polyhydroxyalkyl, aryl, pyridyl, alkenyl, alkynyl, allenyl, formyl, acyl, aminoacyl, carboxy or alkoxyacyl;
R$^a$ and R$^b$ are independently hydrogen, alkyl, aryl, ammonium, tetraalkyl ammonium or a metal cation,
wherein at least: R$^3$ is aryl; or R$^4$ is furyl, thienyl, pyrrolyl, benzofuryl, or benzothienyl; or R$^6$ is hydroxyalkyl, polyhydroxyalkyl, or 2-pyridyl.

2. The compound of claim 1, wherein R$^2$ is hydrogen or alkyl.

3. The compound of claim 1, wherein R$^3$ is hydrogen, alkyl or aryl.

4. The compound of claim 1, wherein R$^4$ is aryl, furyl, thienyl, pyrrolyl, benzofuryl, or benzothienyl.

5. The compound of claim 1, wherein R$^4$ is furyl, thienyl, pyrrolyl, benzofuryl, or benzothienyl.

6. The compound of claim 1, wherein R$^4$ is selected from furyl and thienyl.

7. The compound of claim 1, wherein R$^5$ is hydrogen.

8. The compound of claim 1, wherein R$^6$ is carboxy.

9. The compound of claim 1, wherein R$^6$ is hydroxyalkyl or polyhydroxyalkyl.

10. The compound of claim 1, wherein R$^6$ is 2-pyridyl.

11. The compound of claim 1, wherein R$^a$ and R$^b$ are each independently hydrogen or alkyl.

12. A compound having a general formula selected from a group consisting of:

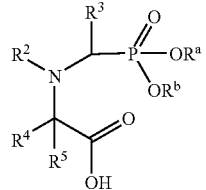 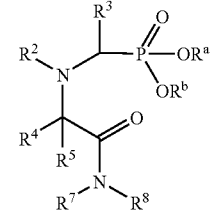

wherein:
R$^2$ is hydrogen, alkyl, allyl, aryl, acyl, sulfonyl, amino, alkylamino, dialkylamino, acylamino, sulfonylamino, or alkoxy;
R$^3$ is hydrogen, alkyl, alkenyl, or aryl;
R$^4$ is alkyl, aryl, furyl, thienyl, pyrrolyl, benzofuryl, benzothienyl, allyl, alkenyl, alkynyl, or allenyl;
R$^5$ is hydrogen, alkyl, or aryl;
R$^7$ and R$^8$ are independently hydrogen, alkyl, allyl, aryl, hydroxyl, alkoxy, aryloxy, acyl, sulfonyl, amino, alkylamino, dialkylamino, acylamino, sulfonylamino or alkoxy;
R$^a$ and R$^b$ are independently hydrogen, alkyl, aryl, ammonium, tetraalkyl ammonium or a metal cation.
wherein at least: R$^3$ is aryl; or R$^4$ is furyl, thienyl, pyrrolyl, benzofuryl, or benzothienyl.

13. The compound of claim 12, wherein R$^2$ is hydrogen or alkyl.

14. The compound of claim 12, wherein R$^3$ is hydrogen, alkyl or aryl.

15. The compound of claim 12, wherein R$^4$ is aryl, furyl, thienyl, pyrrolyl, benzofuryl, or benzothienyl.

16. The compound of claim 12, wherein R$^4$ is furyl, thienyl, pyrrolyl, benzofuryl or benzothienyl.

17. The compound of claim 12, wherein $R^5$ is hydrogen.

18. The compound of claim 12, wherein $R^a$ and $R^b$ are each independently hydrogen or alkyl.

19. The compound of claim 12, wherein $R^a$ and $R^b$ are alkyl.

20. A compound having a general formula:

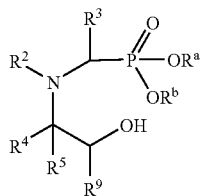

wherein:
- $R^2$ is hydrogen, alkyl, allyl, aryl, acyl, sulfonyl, amino, alkylamino, dialkylamino, acylamino, sulfonylamino, or alkoxy;
- $R^3$ is hydrogen, alkyl, alkenyl, or aryl;
- $R^4$ is alkyl, aryl, furyl, thienyl, pyrrolyl, benzofuryl, benzothienyl, allyl, alkenyl, alkynyl, or allenyl;
- $R^5$ is hydrogen, alkyl, or aryl;
- $R^9$ is hydrogen, alkyl, aryl, alkenyl, alkynyl, allenyl, hydroxyalkyl, or polyhydroxyalkyl;
- $R^a$ and $R^b$ are independently hydrogen, alkyl, aryl, ammonium, tetraalkyl ammonium or a metal cation.

21. The compound of claim 20, wherein $R^2$ is hydrogen or alkyl.

22. The compound of claim 20, wherein $R^3$ is hydrogen, alkyl or aryl.

23. The compound of claim 20, wherein $R^4$ is aryl, furyl, thienyl, pyrrolyl, benzofuryl, or benzothienyl.

24. The compound of claim 20, wherein $R^4$ is furyl, thienyl, pyrrolyl, benzofuryl or benzothienyl.

25. The compound of claim 20, wherein $R^5$ is hydrogen.

26. The compound of claim 20, wherein $R^a$ and $R^b$ are each independently hydrogen or alkyl.

27. The compound of claim 20, wherein $R^9$ is hydroxyalkyl or polyhydroxyalkyl.

28. A compound having a general formula:

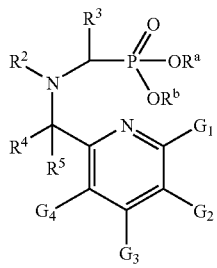

wherein:
- $R^2$ is hydrogen, alkyl, allyl, aryl, acyl, sulfonyl, amino, alkylamino, dialkylamino, acylamino, sulfonylamino, or alkoxy;
- $R^3$ is hydrogen, alkyl, alkenyl, or aryl;
- $R^4$ is alkyl, aryl, furyl, thienyl, pyrrolyl, benzofuryl, benzothienyl, allyl, alkenyl, alkynyl, or allenyl;
- $R^5$ is hydrogen, alkyl, or aryl;
- $R^a$ and $R^b$ are each independently hydrogen, alkyl, aryl, ammonium, tetraalkyl ammonium or a metal cation;
- $G^1$-$G^4$ are each independently hydrogen, alkyl, aryl, hydroxyl, alkoxy, aryloxy, chloro, bromo, fluoro, dialkylamino, acylamino, or sulfonylamino.

29. The compound of claim 28, wherein $R^2$ is hydrogen or alkyl.

30. The compound of claim 28, wherein $R^3$ is hydrogen, alkyl or aryl.

31. The compound of claim 28, wherein $R^4$ is aryl, furyl, thienyl, pyrrolyl, benzofuryl, or benzothienyl.

32. The compound of claim 28, wherein $R^4$ is furyl, thienyl, pyrrolyl, benzofuryl or benzothienyl.

33. The compound of claim 28, wherein $R^5$ is hydrogen.

34. The compound of claim 28, wherein $R^a$ and $R^b$ are each independently hydrogen or alkyl.

35. The compound of claim 28, wherein $G^1$-$G^4$ are hydrogen.

36. A compound of general formula:

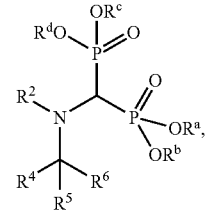

wherein:
- $R^2$ is hydrogen, alkyl, allyl, aryl, acyl, sulfonyl, amino, alkylamino, dialkylamino, acylamino, sulfonylamino, or alkoxy;
- $R^4$ is alkyl, aryl, furyl, thienyl, pyrrolyl, benzofuryl, benzothienyl, allyl, alkenyl, alkynyl, or allenyl;
- $R^5$ is hydrogen, alkyl, hydroxyalkyl, polyhydroxyalkyl, aryl, alkenyl, alkynyl, allenyl, formyl, acyl, aminoacyl, carboxy or alkoxyacyl;
- $R^6$ is hydrogen, alkyl, hydroxyalkyl, polyhydroxyalkyl, aryl, pyridyl, alkenyl, alkynyl, allenyl, formyl, acyl, aminoacyl, carboxy or alkoxyacyl;
- $R^a$-$R^d$ are each independently hydrogen, alkyl, aryl, ammonium, tetraalkyl ammonium or a metal cation.

37. The compound of claim 36, wherein $R^2$ is hydrogen or alkyl.

38. The compound of claim 36, wherein $R^4$ is aryl, furyl, thienyl, pyrrolyl, benzofuryl, or benzothienyl.

39. The compound of claim 36, wherein $R^4$ is furyl, thienyl, pyrrolyl, benzofuryl or benzothienyl.

40. The compound of claim 36, wherein $R^5$ is hydrogen.

41. The compound of claim 36, wherein $R^a$-$R^d$ are each independently hydrogen or alkyl.

42. A compound having a general formula selected from a group consisting of:

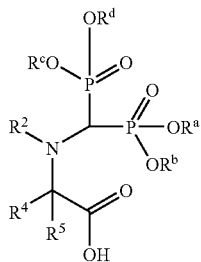
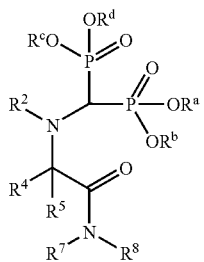

wherein:
- $R^2$ is hydrogen, alkyl, allyl, aryl, acyl, sulfonyl, amino, alkylamino, dialkylamino, acylamino, sulfonylamino, or alkoxy;
- $R^4$ is alkyl, aryl, furyl, thienyl, pyrrolyl, benzofuryl, benzothienyl, allyl, alkenyl, alkynyl, or allenyl;
- $R^5$ is hydrogen, alkyl, or aryl;
- $R^7$ and $R^8$ are each independently hydrogen, alkyl, allyl, aryl, hydroxyl, alkoxy, aryloxy, acyl, sulfonyl, amino, alkylamino, dialkylamino, acylamino, sulfonylamino or alkoxy;
- $R^a$-$R^d$ are independently hydrogen, alkyl, aryl, ammonium, tetraalkyl ammonium or a metal cation.

43. The compound of claim 42, wherein $R^2$ is hydrogen or alkyl.

44. The compound of claim 42, wherein $R^4$ is aryl, furyl, thienyl, pyrrolyl, benzofuryl, or benzothienyl.

45. The compound of claim 42, wherein $R^4$ is furyl, thienyl, pyrrolyl, benzofuryl or benzothienyl.

46. The compound of claim 42, wherein $R^5$ is hydrogen.

47. The compound of claim 42, wherein $R^a$-$R^d$ are each independently hydrogen or alkyl.

48. A compound having a general formula:

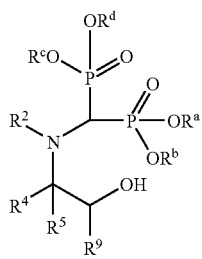

wherein:
- $R^2$ is hydrogen, alkyl, allyl, aryl, acyl, sulfonyl, amino, alkylamino, dialkylamino, acylamino, sulfonylamino, or alkoxy;
- $R^4$ is alkyl, aryl, furyl, thienyl, pyrrolyl, benzofuryl, benzothienyl, allyl, alkenyl, alkynyl, or allenyl;
- $R^5$ is hydrogen, alkyl, or aryl;
- $R^9$ is hydrogen, alkyl, aryl, alkenyl, alkynyl, allenyl, hydroxyalkyl, or polyhydroxyalkyl;
- $R^a$-$R^d$ are independently selected from a group consisting of hydrogen, alkyl, aryl, ammonium, tetraalkyl ammonium or a metal cation.

49. The compound of claim 48, wherein $R^2$ is hydrogen or alkyl.

50. The compound of claim 48, wherein $R^4$ is aryl, furyl, thienyl, pyrrolyl, benzofuryl, or benzothienyl.

51. The compound of claim 48, wherein $R^4$ is furyl, thienyl, pyrrolyl, benzofuryl or benzothienyl.

52. The compound of claim 48, wherein $R^5$ is hydrogen.

53. The compound of claim 48, wherein $R^a$-$R^d$ are each independently hydrogen or alkyl.

54. The compound of claim 48, wherein $R^9$ is hydroxyalkyl or polyhydroxyalkyl.

55. A compound having a general formula:

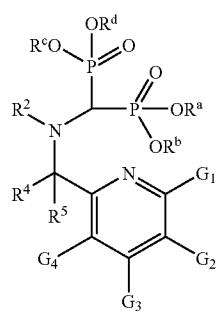

wherein:
- $R^2$ is hydrogen, alkyl, allyl, aryl, acyl, sulfonyl, amino, alkylamino, dialkylamino, acylamino, sulfonylamino, or alkoxy;
- $R^4$ is alkyl, aryl, furyl, thienyl, pyrrolyl, benzofuryl, benzothienyl, allyl, alkenyl, alkynyl, or allenyl;
- $R^5$ is hydrogen, alkyl, or aryl;
- $R^a$-$R^d$ are independently hydrogen, alkyl, aryl, ammonium, tetraalkyl ammonium or a metal cation;
- $G^1$-$G^4$ are independently hydrogen, alkyl, aryl, hydroxyl, alkoxy, aryloxy, chloro, bromo, fluoro, dialkylamino, acylamino, or sulfonylamino.

56. The compound of claim 55, wherein $R^2$ is hydrogen or alkyl.

57. The compound of claim 55, wherein $R^4$ is aryl, furyl, thienyl, pyrrolyl, benzofuryl, or benzothienyl.

58. The compound of claim 55, wherein $R^4$ is furyl, thienyl, pyrrolyl, benzofuryl or benzothienyl.

59. The compound of claim 55, wherein $R^5$ is hydrogen.

60. The compound of claim 55, wherein $R^a$-$R^d$ are hydrogen or alkyl.

61. The compound of claim 55, wherein $G^1$-$G^4$ are hydrogen.

62. A method for the preparation of an amino phosphonate of the general formula:

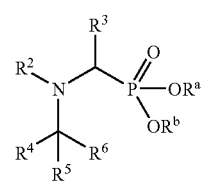

by reacting:
an amino phosphonate of formula

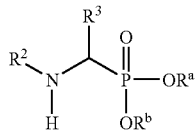

a carbonyl compound of formula

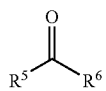

and an organoboron compound of formula

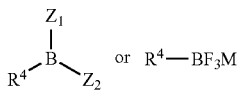

wherein:
$R^2$ is hydrogen, alkyl, allyl, aryl, acyl, sulfonyl, amino, alkylamino, dialkylamino, acylamino, sulfonylamino, or alkoxy;

$R^3$ is hydrogen, alkyl, alkenyl, aryl, phosphonic acid, phosphonate or phosphonamido;

$R^4$ is alkyl, aryl, furyl, thienyl, pyrrolyl, benzofuryl, benzothienyl, allyl, alkenyl, alkynyl, or allenyl;

$R^5$ is hydrogen, alkyl, or aryl;

$R^6$ is hydrogen, alkyl, hydroxyalkyl, polyhydroxyalkyl, aryl, pyridyl, alkenyl, alkynyl, allenyl, formyl, acyl, aminoacyl, carboxy or alkoxyacyl;

$R^a$ and $R^b$ are independently hydrogen, alkyl, aryl, ammonium, tetraalkyl ammonium or a metal cation;

$Z^1$ and $Z^2$ are independently hydroxyl, alkoxy, aryloxy, amino or sulfonylamino, provided that $Z^1$ and $Z^2$ can also be joined together forming a ring; and M is a cation selected from a group consisting of the cations of: potassium, sodium, lithium, cesium, magnesium, ammonium, tetraalkyl ammonium and aryl-alkyl ammonium, wherein at least: $R^3$ is aryl; or $R^4$ is furyl, thienyl, pyrrolyl, benzofuryl, or benzothienyl; or $R^6$ is hydroxyalkyl, polyhydroxyalkyl, or 2-pyridyl.

63. The method of claim 62 wherein $R^2$-$R^6$, $R^a$ or $R^b$, $Z^1$ or $Z^2$ is connected to a polymeric chain or other solid phase material.

64. The method of claim 62 wherein $R^3$ is hydrogen, alkyl, alkenyl, or aryl.

65. The method of claim 62 wherein $R^3$ is phosphonic acid, phosphonate or phosphonamido.

66. A pharmaceutical composition, comprising: a compound according to claim 1 and a pharmaceutically acceptable carrier.

* * * * *

UNITED STATES PATENT AND TRADEMARK OFFICE
CERTIFICATE OF CORRECTION

PATENT NO. : 7,420,000 B2
APPLICATION NO. : 10/938256
DATED : September 2, 2008
INVENTOR(S) : Nicos A. Petasis It is certified that error appears in the above-identified patent and that said Letters Patent is hereby corrected as shown below:

Title Page; item (56);

On the Cover Page, Other Publications; replace:
  "to new Bone Antiresportion and Antiparasitic Agents", Journal of" with
  -- to new Bone Antiresorption and Antiparasitic Agents", Journal of --

On the Cover Page, Other Publications; replace:
  "Petasis, N. A. et al., "Synthesis of prperazinones and" with
  -- Petasis, N. A. et al., "Synthesis of piperazinones and --

Column 34, Line 57 at Claim 12; replace:
  "ammonium or a metal cation." with
  -- ammonium or a metal cation --

Column 36, Lines 30-40; replace the chemical compound with:

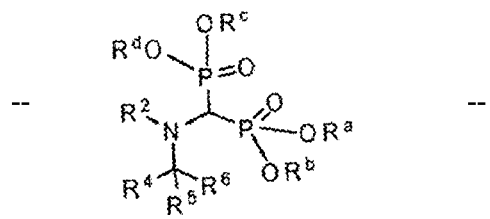

Signed and Sealed this

Third Day of March, 2009

JOHN DOLL
*Acting Director of the United States Patent and Trademark Office*